United States Patent
Kinooka et al.

(10) Patent No.: US 10,954,487 B2
(45) Date of Patent: Mar. 23, 2021

(54) CELL CULTURING METHOD (71) Applicant: Osaka University, Osaka (JP)

(72) Inventors: Masahiro Kinooka, Osaka (JP); Eiji Nagamori, Osaka (JP)

(73) Assignee: Osaka University, Osaka (JP)

( * ) Notice: Subject to any disclaimer, the term of this patent is extended or adjusted under 35 U.S.C. 154(b) by 79 days.

(21) Appl. No.: 16/071,969

(22) PCT Filed: Jan. 20, 2017

(86) PCT No.: PCT/JP2017/001874
§ 371 (c)(1),
(2) Date: Jul. 23, 2018

(87) PCT Pub. No.: WO2017/126647
PCT Pub. Date: Jul. 27, 2017

(65) Prior Publication Data
US 2019/0032006 A1    Jan. 31, 2019

(30) Foreign Application Priority Data

Jan. 21, 2016 (JP) .............................. JP2016-010050

(51) Int. Cl.
C12N 5/00     (2006.01)
C12M 1/00     (2006.01)
C12N 5/074    (2010.01)
C12M 1/04     (2006.01)
C12M 1/34     (2006.01)
C12N 5/0735   (2010.01)

(52) U.S. Cl.
CPC ............. C12N 5/0018 (2013.01); C12M 1/04 (2013.01); C12M 23/14 (2013.01); C12M 23/28 (2013.01); C12M 29/06 (2013.01); C12M 41/44 (2013.01); C12N 5/0606 (2013.01); C12N 5/0607 (2013.01); C12N 5/0696 (2013.01); C12N 2500/05 (2013.01); C12N 2501/727 (2013.01); C12N 2527/00 (2013.01); C12N 2533/54 (2013.01); C12N 2533/90 (2013.01)

(58) Field of Classification Search
None
See application file for complete search history.

(56) References Cited

U.S. PATENT DOCUMENTS

| | | |
|---|---|---|
| 2013/0099398 A1 | 4/2013 | Takase et al. |
| 2014/0191425 A1 | 7/2014 | Yano et al. |
| 2015/0140652 A1 | 5/2015 | Sasai et al. |
| 2017/0056438 A1 | 3/2017 | Kamei |

FOREIGN PATENT DOCUMENTS

| | | | |
|---|---|---|---|
| EP | 2878664 A1 | 6/2015 | |
| JP | H07-008264 A | 1/1995 | |
| JP | 2010-253372 A | 11/2010 | |
| JP | 2011-019513 A | 2/2011 | |
| JP | 2011-078371 A | 4/2011 | |
| JP | 2012-172055 A | 9/2012 | |
| JP | 2014-223087 A | 12/2014 | |
| JP | 2015-126719 A | 7/2015 | |
| WO | 2007/015770 A1 | 2/2007 | |
| WO | 2012/005018 A1 | 1/2012 | |
| WO | 2013/088667 A1 | 6/2013 | |
| WO | 2013/183777 A1 | 12/2013 | |
| WO | 2014/017513 A1 | 1/2014 | |
| WO | 2015/099201 A1 | 7/2015 | |

OTHER PUBLICATIONS

Tahara et al., "The development and implementation of a new bioreactor named "VerSus Reactor" for mammalian cell culture," Pharm Tech Japan, 31: 2641-2649 (2015).
Castillo et al., "Transfer of Hepatic Progenitor Stem Cell Culture Process from Multiple Tracy Stacks to the Xpansion Multiplate Bioreactor," Cytotherapy, Supplement S20 (2013).
Merten, "Advances in cell culture: anchorage dependence," Philosophical Transactions B, 370: 20140040 (2015).
Brophy et al., "Rat hepatocyte spheroids formed by rocked technique maintain differentiated hepatocyte gene expression and function," Hepatology, 49: 578-586 (2009).
Mori et al., "Effect of Neurosphere Size on the Growth Rate of Human Neural Stem/Progenitor Cells," Journal of Neuroscience Research, 84: 1682-1691 (2006).
Lam et al., "Integrated processes for expansion and differentiation of human pluripotent stem cells in suspended microcarriers cultures," Biochemical and Biophysical Research Communications, 473: 764-768 (2016).
Serra et al., "Microencapsulation Technology: A Powerful Tool for Integrating Expansion and Cryopreservation of Human Embryonic Stem Cells," PLoS One, 6: e23212 (2011).
Matsunaga et al., "Culture scale-up studies as seen from the viewpoint of oxygen supply and dissolved carbon dioxide stripping," Journal of Bioscience and Bioengineering, 107: 412-418 (2009).
Marks, "Equipment design considerations for large scale cell culture," Cytotechnology, 42: 21-33 (2003).
Kempf et al., "Controlling Expansion and Cardiomyogenic Differentiation of Human Pluripotent Stem Cells in Scalable Suspension Culture," Stem Cell Reports, 3: 1132-1146 (2014).
Singh, Disposable bioreactor for cell culture using wave-induced agitation, Cytotechnology, 30: 149-158 (1999).
Correia et al., "Combining Hypoxia and Bioreactor Hydrodynamics Boosts Induced Pluripotent Stem Cell Differentiation Towards Cardiomyocytes," Stem Cell Reviews and Reports, 10: 786-801 (2014).

(Continued)

Primary Examiner — Blaine Lankford
(74) Attorney, Agent, or Firm — Morgan, Lewis & Bockius LLP (57) ABSTRACT Provided is a cell culturing method in which physical stress is reduced and oxygen can be supplied. The invention relates to a cell culturing method including; arranging cells in a dispersed state in a culture medium which is a plastic fluid; and introducing air bubbles into said culture medium.

6 Claims, 5 Drawing Sheets (56) References Cited

OTHER PUBLICATIONS

Lei et al., "Developing Defined and Scalable 3D Culture Systems for Culturing Human Pluripotent Stem Cells at High Densities," Cellular and Molecular Bioengineering, 7: 172-183 (2014).

Moon et al., "Optimizing human embryonic stem cells differentiation efficiency by screening size-tunable homogenous embryoid bodies," BIomaterials, 35: 5987-5997 (2014).

Otsuji et al., "A 3D Sphere Culture System Containing Functional Polymers for Large-Scale Human Pluripotent Stem Cell Production," Stem Cell Reports, 2: 1-12 (2014).

International Search Report issued in corresponding International Patent Application No. PCT/JP2017/001874 dated Apr. 25, 2017.

Normal Culture Medium

Plastic Fluid Culture Medium

FIG. 1

Normal Culture Medium

Plastic Fluid Culture Medium

FIG. 2

Vicinity of Air Bubble Generating Portion

FIG. 3

Position Away from Air Bubble Generating Portion

CELL CULTURING METHOD

TECHNICAL FIELD

The present disclosure relates to a cell culturing method using a plastic fluid.

BACKGROUND ART

In regenerative medicine using human iPS (induced pluripotent stem) cells, utilization of techniques using animal cells such as antibody drug production using CHO (Chinese Hamster Ovary) cells has been promoted. Compared to two-dimensional plate culture, three-dimensional culture in which cells are cultured in a suspension state can increase the cell concentration per unit volume and thereby has advantages such as space saving and a reduction in the amount of the culture medium to be used.

On the other hand, in culture in which a high cell concentration has been achieved, the oxygen consumption rate of the cells is high, which causes limitation in oxygen supply in the culture solution. The concentration of oxygen that can be dissolved in the solution at normal temperature and normal pressure is about 7 to 8 mg/L. Oxygen can be said to be a nutritional component that cannot be maintained at a sufficiently high concentration in the solution.

Examples of the method of increasing the supply (mass transfer) of oxygen from the gas phase to the liquid phase include increasing the area of the gas-liquid contact surface. In culturing robust cells such as microorganisms, aeration (bubbling) of the culture medium with small bubbles crashed using, for example, a sparger can be performed. However, in animal cells in general, their resistance to shear stress is not sufficiently high and therefore bubbling cannot be applied.

Some other methods have been proposed in which there are provided structures that prevent bubbles from being generated or bubbles and cells from contacting with each other. Basically, however, aeration by bubbling in animal cell culture has not been achieved.

Generally, aeration in animal cell culture, mainly in a small culture tank, is performed by a surface aeration method that relies on the oxygen transfer at the gas-liquid interface of the culture solution, and by a method in which a hydrophobic membrane tubes are arranged in the culture medium to increase the gas-liquid interfacial area per unit volume. However, in the former method, the gas-liquid interfacial area per unit volume decreases as the amount of the culture solution increases. Therefore, it is difficult to apply the former method to the culture in which a culture medium is used in a large volume such as several to several tens of liters or more. Furthermore, in the latter method, since the culture tank has a complicated innerstructure, it is expected that the risk of contamination may increase, which is considered to be impractical.

On the other hand, Patent Document 1 discloses a culture medium composition containing a polymer compound having an anionic functional group or a polysaccharide, as a culture medium in which cells can be cultured while being maintained in a suspended state without being stirred.

PRIOR ART DOCUMENTS

Patent Documents

[Patent Document 1] WO2014/017513

SUMMARY

Technical Problem

As described above, basically, aeration by bubbling in animal cell culture has not been achieved. In the case of CHO cells, an example of bubbling into a large culture tank is also known, but this is a condition that allows shear stress damages to the cells to some extent. In culturing cells that are used, for example, for regenerative medicine, it is preferable that the physical stress on the cells be small. In addition, culture media for regenerative medicine have a higher concentration of protein contained therein as compared to culture media for CHO cells, and thereby foaming by bubbling becomes a problem.

In one or more embodiments, the present disclosure provides a cell culturing method in which physical stress is reduced and oxygen can be supplied.

Solution to Problem

In one aspect, the present disclosure relates to a cell culturing method including arranging cells in a culture medium which is a plastic fluid and introducing air bubbles into said culture medium.

Effects of the Invention

In one or more embodiments, the cell culturing method according to the present disclosure makes it possible to perform suspended cell culture in which both a suppression of physical stress on cells and an improvement in oxygen supply are achieved. Furthermore, in one or more embodiments, the cell culturing method according to the present disclosure makes it possible to achieve both a suppression of physical stress on cells and an improvement in oxygen supply even in the suspended cell culture using a large volume of culture medium, which makes it possible to mass-culture cells that are sensitive to physical stress, such as cells that are used for regenerative medicine and plant cells.

DESCRIPTION OF EMBODIMENTS

The present disclosure is based on the knowledge that incorporating an oxygen supply method of introducing air bubbles into a plastic fluid makes it possible to perform suspended cell culture in which both a suppression of physical stress on cells and an improvement in oxygen supply are achieved.

The mechanism in which incorporating an oxygen supply method of introducing air bubbles into a plastic fluid makes it possible to perform suspended cell culture in which both a suppression of physical stress on cells and an improvement in oxygen supply are achieved is presumed as follows.

By using a plastic fluid, cells are maintained in the fluid without sedimenting. For example, cells are maintained in a suspended state, or when cells are dispersed, the cells are maintained in a dispersed state. This eliminates the need for stirring to suspend the cells, resulting in elimination of physical stress.

The rising speed of the air bubbles introduced into the plastic fluid is suppressed. This means that the residence time of the air bubbles in the plastic fluid is extended and gas holdup increases.

When the residence time of the air bubbles is extended, the oxygen supply amount (mass transfer) per air bubble increases, the aeration amount can be reduced, and the physical stress caused by convection and foaming is suppressed.

As the gas holdup increases, the apparent dissolved oxygen amount per unit culture medium increases, enabling high-concentration cell culture.

The movement of the air bubbles introduced into the plastic fluid is temporary and local flow. The plastic fluid does not flow except for an air bubble rising portion, and the convection caused by the rising of the air bubbles is also suppressed. As a result, an environment in which physical stress, such as shear stress, is suppressed is maintained.

However, the present disclosure may not be construed as being limited to these mechanisms.

[Plastic Fluid]

In the present disclosure, the plastic fluid is a fluid that requires a yield stress to flow, that is, a fluid having a yield value. The plastic fluid may be a Bingham fluid or a non-Bingham fluid. In the present disclosure, the plastic fluid refers to one that can maintain cells in said plastic fluid without allowing them to sediment in a static state.

[Culture Medium which is Plastic Fluid]

In the present disclosure, the culture medium which is a plastic fluid refers to a plastic fluid containing a culture medium component and a specific compound, and in one or more non-limiting embodiments, examples thereof include a plastic fluid formed of a liquid culture medium and a specific compound that are mixed together.

The culture medium component and the liquid culture medium to be used can be a culture medium component and a liquid culture medium that can be generally used depending on the cells to be cultured by the method according to the present disclosure.

The above-mentioned specific compound is a compound that can convert a liquid or a culture medium, which is not a plastic fluid, into a plastic fluid. In one or more non-limiting embodiments, one disclosed in WO2014/017513 can be used.

[Specific Compound for Forming Plastic Fluid]

The specific compound for forming a plastic fluid is not particularly limited. Examples thereof include a polymer compound, preferably a polymer compound having an anionic functional group.

Examples of the anionic functional group include a carboxy group, a sulfo group, a phosphoric acid group, and salts thereof, and a carboxy group or a salt thereof is preferred.

The above-mentioned polymer compound to be used can be one having one type or two or more types selected from the group consisting of the anionic functional groups.

Preferred specific examples of the specific compound for forming a plastic fluid are not particularly limited. Examples thereof include polysaccharides in which at least ten monosaccharides (for example, trioses, tetroses, pentoses, hexoses, or heptoses) are polymerized, more preferably an acidic polysaccharide having an anionic functional group. The acidic polysaccharide referred to herein is not particularly limited as long as it has an anionic functional group in its structure. Examples thereof include polysaccharides having uronic acid (for example, glucuronic acid, iduronic acid, galacturonic acid, or mannuronic acid), polysaccharides each having a sulfate group or a phosphate group in a part of its structure, or polysaccharides having both structures thereof, which include not only naturally occurring polysaccharides but also polysaccharides produced by microorganisms and polysaccharides produced by genetic engineering, or polysaccharides artificially synthesized using enzymes. More specifically, examples of the acidic polysaccharide include those composed of one type or two or more types selected from the group consisting of hyaluronic acid, gellan gum, deacylated gellan gum (hereinafter may be referred to as DAG), rhamsan gum, diutan gum, xanthan gum, carrageenan, zanthan gum, hexuronic acid, fucoidan, pectin, pectic acid, pectinic acid, heparan sulfate, heparin, heparitin sulfate, keratosulfate, chondroitin sulfate, dermatan sulfate, rhamnan sulfate, and salts thereof. The polysaccharides are preferably hyaluronic acid, DAG, diutan gum, xanthan gum, carrageenan, or a salt thereof, and more preferably DAG from the viewpoints that the DAG can be used at a low concentration to allow cells or tissues to be suspended and makes it easy to recover the cells or tissues. Examples of the salt referred to herein include a salt of an alkali metal such as lithium, sodium, or potassium, a salt of an alkaline earth metal such as calcium, barium, or magnesium, or a salt of, for example, aluminum, zinc, steel, iron, ammonium, organic base, or amino acid.

The weight average molecular weight of these polymer compounds (for example, polysaccharides) is preferably 10,000 to 50,000,000, more preferably 100,000 to 20,000,000, and further preferably 1,000,000 to 10,000,000. For example, said molecular weight can be measured in terms of pullulan by gel permeation chromatography (GPC). Furthermore, DAG to be used can be one phosphorylated. This phosphorylation can be carried out by a known method.

In one or more embodiments, a plurality of types (preferably two types) of the above-mentioned polysaccharides can be used in combination. The type of the combination of polysaccharides is not particularly limited but preferably the combination includes at least DAG or a salt thereof. That is, examples of suitable combinations of polysaccharides include DAG or a salt thereof and polysaccharide (for example, xanthan gum, alginic acid, carrageenan, diutan gum, methylcellulose, locust bean gum, or a salt thereof) other than DAG or a salt thereof. Examples of specific combinations of polysaccharides include, but are not limited to, DAG and rhamsan gum, DAG and diutan gum, DAG and xanthan gum, DAG and carrageenan, DAG and zanthan gum, DAG and locust bean gum, DAG and κ-carrageenan, DAG and sodium alginate, as well as DAG and methylcellulose.

More preferable specific examples of the above-mentioned specific compound for forming a plastic fluid include hyaluronic acid, deacylated gellan gum, diutan gum, carrageenan, and xanthan gum as well as salts thereof, and preferred examples thereof include deacylated gellan gum or a salt thereof. In the present disclosure, the deacylated gellan gum refers to a linear high molecular weight polysaccharide having, as a structural unit thereof, a sugar composed of four molecules including 1,3-linked glucose, 1,4-linked glucuronic acid, 1,4-linked glucose, and 1,4-linked rhamnose, which is a polysaccharide represented by General Formula (I) below, where $R_1$ and $R_2$ are both hydrogen atoms and n is an integer of 2 or more. However, $R_1$ may contain a glyceryl group and $R_2$ may contain an acetyl group, but the contents of the acetyl group and the glyceryl group are preferably 10% or less, more preferably 1% or less.

viscosity of the culture medium which is a plastic fluid is not particularly limited and may be higher than the above-mentioned values.

The specific compound for forming a plastic fluid can be obtained by a chemical synthesis method. However, when said compound is a natural product, it is preferable to obtain the compound by extracting it from various plants, various animals, or various microorganisms containing it and then separating and purifying it using conventional techniques. In extracting it, when water or a supercritical gas is used, said compound can be efficiently extracted. For example, a method for producing gellan gum may be as follows: gellan gum-producing microorganisms are cultured in a fermentation medium, and a mucosa product produced outside the bacterial cells is recovered by a common purification method and then is made into a powder form after some steps of, for example, drying and pulverizing it. Furthermore, in the case of deacylated gellan gum, when the mucosa product is recovered, it may be subjected to an alkaline treatment to deacylate the glyceryl group and acetyl group linked to 1,3-linked glucose residue and then may be recovered. For the purification method, for example, liquid-liquid extraction, fractional precipitation, crystallization, various ion exchange chromatography, gel filtration chromatography using, for example, Sephadex LH-20, an adsorption/desorption treatment of an active substance by thin-layer chromatography or adsorption chromatography using, for example, activated carbon or silica gel, or high performance liquid chromatography using a reversed-phase column can be used alone or in combination in an arbitrary order or repeatedly to remove impurities and thus purification is carried out. Examples of gellan gum-producing microorganisms include, but are not limited to, *Sphingomonas elodea* and microorganisms in which the gene of said microorganism has been modified.

In the case of deacylated gellan gum, commercially available products such as "KELCOGEL (registered trademark of CP Kelco) CG-LA" manufactured by SANSHO Co., Ltd. or "KELCOGEL (registered trademark of CP Kelco)" manufactured by San-Ei Gen F.F.I., Inc. can be (I)

There are various mechanisms by which a plastic fluid is formed with the above-mentioned specific compound. In the case of using deacylated gellan gum, when mixed with a liquid culture medium, the deacylated gellan gum takes in metal ions (for example, calcium ions) contained in the liquid culture medium to form an amorphous structure through said metal ions and thereby suspends cells and/or tissues. In one or more embodiments, the viscosity of a culture medium which is a plastic fluid that is prepared from deacylated gellan gum is 8 mPa·s or less, preferably 4 mPa·s or less, and it is more preferably 2 mPa·s or less in view of the ease of recovery of cells or tissues. However, in the cell culturing method according to the present disclosure, the used. Furthermore, as a native-type gellan gum, for example, "KELCOGEL (registered trademark of CP Kelco) HT" manufactured by San-Ei Gen F.F.I., Inc. can be used.

[Concentration of Specific Compound in Culture Medium which is Plastic Fluid]

The concentration (mass/volume %, hereinafter simply referred to as "%") of the aforementioned specific compound in the culture medium which is a plastic fluid depends on the type of the specific compound and can be suitably set within the range in which a plastic fluid capable of maintaining cells in the culture medium without allowing them to sediment in a static state can be formed. The concentration is usually 0.0005% to 1.0%, preferably 0.001% to 0.4%, more preferably 0.005% to 0.1%, and further preferably 0.005% to 0.05%. For example, in the case of deacylated gellan gum, the concentration thereof is 0.001% to 1.0%, preferably 0.003% to 0.5%, more preferably 0.005% to 0.1%, further preferably 0.01% to 0.05%, and further more preferably 0.02% to 0.05%. In the case of xanthan gum, the concentration thereof is 0.001% to 5.0%, preferably 0.01% to 1.0%, more preferably 0.05% to 0.6%, and further more preferably 0.3% to 0.6%. In the case of κ-carrageenan and locust bean gum mixtures, the concentration thereof is 0.001% to 5.0%, preferably 0.005% to 1.0%, more preferably 0.01% to 0.1%, and most preferably 0.03% to 0.05%. In the case of native-type gellan gum, the concentration thereof is 0.05% to 1.0%, preferably 0.05% to 0.1%.

In the case where a plurality of types (preferably two types) of the aforementioned polysaccharides are used in combination, the concentration of said polysaccharides can be suitably set within the range in which a plastic fluid capable of maintaining cells in the culture medium without allowing them to sediment in a static state can be formed. For example, when a combination of DAG or a salt thereof and a polysaccharide other than DAG or a salt thereof is used, the concentration of DAG or a salt thereof is, for example, 0.005 to 0.02%, preferably 0.01 to 0.02%, and the concentration of the polysaccharide other than DAG or a salt thereof is, for example, 0005 to 0.4%, preferably 0.1 to 0.4%. Combinations of specific concentration ranges are, for example, as follows.

DAG or a salt thereof: 0.005 to 0.02% (preferably 0.01 to 0.02%)
Polysaccharides other than DAG
Xanthan gum: 0.1 to 0.4%
Sodium alginate: 0.1 to 0.4%
Locust bean gum: 0.1 to 0.4%
Methylcellulose: 0.1 to 0.4% (preferably 0.2 to 0.4%)
Carrageenan: 0.05 to 0.1%
Diutan gum: 0.05 to 0.1%

Said concentration can be calculated by the following formula:

Concentration (%)=Mass of Specific Compound (g)/
Volume of Culture Medium (ml)×100

The specific compound can be further converted to another derivative by a chemical synthesis method and said derivative thus obtained can also be effectively used in the cell culturing method according to the present disclosure. Specifically, in the case of deacylated gellan gum, derivatives obtained by replacing the hydroxyl group corresponding to $R_1$ and/or $R_2$ of the compound represented by General Formula (I) above with, for example, C1-3 alkoxy group, C1-3 alkylsulfonyl group, a monosaccharide residue such as glucose or fructose, an oligosaccharide residue such as sucrose or lactose, or an amino acid residue such as glycine or arginine can also be used in the present invention. Furthermore, said compound can also be crosslinked using a crosslinker such as 1-ethyl-3-(3-di-methylaminopropyl) carbodiimide (EDC).

The specific compound or a salt thereof can be present in any crystal form depending on the production conditions and can be present as any hydrate. Such crystal forms and hydrates as well as mixtures thereof are also included within the scope of the present invention. Furthermore, it may be present as a solvate containing an organic solvent such as acetone, ethanol, or tetrahydrofuran. These forms are all included within the scope of the cell culturing method according to the present disclosure.

The specific compound that is used in the cell culturing method according to the present disclosure may be present in the form of tautomers, geometric isomers, a mixture of tautomers or geometric isomers, or a mixture thereof, each of which is produced by cyclic or exocyclic isomerization. In the present disclosure, the specific compound may be present in the form of divided optical isomers or a mixture containing them at any ratio when having an asymmetric center regardless of whether it is produced by isomerization or not.

In the culture medium that is used for the cell culturing method according to the present disclosure, metal ions such as divalent metal ions (such as calcium ions, magnesium ions, zinc ions, iron ions, and copper ions) may be present. Preferably, the culture medium contains calcium ions. Said metal ions can be used in combination of two or more types such as calcium ions and magnesium ions, calcium ions and zinc ions, calcium ions and iron ions, or calcium ions and copper ions. Those skilled in the art can suitably determine the combination thereof. In one aspect, when metal ions are contained in the culture medium, polymer compounds aggregate through the metal ions to form a three-dimensional network (for example, polysaccharides form a microgel through metal ions) and thereby a plastic fluid is formed. The concentration of the metal ions can be suitably set within the range in which the specific compound can make a liquid culture medium a plastic fluid capable of maintaining cells in the culture medium without allowing them to sediment in a static state. The salt concentration is 0.1 mM to 300 mM, preferably 0.5 mM to 100 mM, but is not limited thereto. Said metal ions may be mixed with the specific compound together with the liquid culture medium, or a salt solution may be prepared separately to be added to a culture medium in which the specific compound and culture medium component are mixed together.

[Method of Producing Culture Medium which is Plastic Fluid]

In one or more embodiments, the culture medium which is a plastic fluid can be produced by adding a solution or dispersion of the specific compound to a liquid culture medium. The culture medium usually contains metal ions at a concentration sufficient for the specific compound to aggregate through the ions or the specific compound to form a three-dimensional network. Therefore, mere addition of the solution or dispersion of the specific compound to a liquid culture medium can result in a culture medium which is a plastic fluid. Furthermore, a culture medium may be added to the solution or dispersion of the specific compound. Moreover, the culture medium which is a plastic fluid can also be prepared by mixing the specific compound and culture medium component in an aqueous solvent (for example, water such as ion exchanged water, ultrapure water, etc.). Examples of embodiments of mixing include (1) mixing a liquid culture medium and the specific compound (solution), (2) mixing the specific compound (solid such as powder) into a liquid culture medium, (3) mixing a powder culture medium into a solution or dispersion of the specific compound, and (4) mixing a powder culture medium and the specific compound (solid such as powder) with an aqueous solvent, but are not limited thereto. In order to prevent uneven distribution of the specific compound in the culture medium which is a plastic fluid, the embodiment (1) or (4) or the embodiment (1) or (3) is preferred.

[Yield Value of Culture Medium which is Plastic Fluid]

The yield value of the culture medium which is a plastic fluid that is used in the cell culturing method according to the present disclosure is not limited as long as the plastic fluid can maintain cells in the culture medium without allowing them to sediment in a static state. From the viewpoint of maintaining cells, the yield value of the plastic fluid that is used in the cell culturing method according to the present disclosure is preferably at least 0.02 Pa, and from the viewpoint of increasing the gas holdup to improve the viability of cultured cells, it is more preferably at least 0.03 Pa, further preferably at least 0.04 Pa. The yield value of the plastic fluid that is used in the cell culturing method according to the present disclosure is, for example, 0.2 Pa or less or 0.1 Pa or less. The yield value is a value that is measured with a rheometer, and specifically, it is a value that is measured by the method described in Examples.

[Culture Medium]

The culture medium component of the culture medium that is used in the cell culturing method according to the present disclosure can be any culture medium that is used for culturing animal cells when the culture target is cells derived from animals. Examples of such a culture medium include Dulbecco's Modified Eagles's Medium (DMEM), Ham's Nutrient Mixture F12, DMEM/F12 medium, McCoy's 5A Medium, Eagles's Minimum Essential Medium (EMEM), alpha Modified Eagles's Minimum Essential Medium (αMEM), Minimum Essential Medium, RPMI 1640 Medium, Iscove's Modified Dulbecco's Medium (IMDM), MCDB 131 Medium, William's Medium E, IPL 41 Medium, Fischer's Medium, StemPro-34 (manufactured by Invitrogen), X-VIVO 10 (manufactured by Camprex), X-VIVO 15 (manufactured by Cambrex), HMGM (manufactured by Camprex), StemSpan H3000 (manufactured by STEMCELL Technologies Inc.), StemSpan SFEM (manufactured by STEMCELL Technologies Inc.), Stemline II (manufactured by Sigma-Aldrich), QBSF-60 (manufactured by Quality Biological Inc.), StemPro hESC SFM (manufactured by Invitrogen), Essential 8 (registered trademark) Medium (manufactured by Gibco), mTeSR1 or 2 Medium (manufactured by STEMCELL Technologies Inc.), ReproFF or ReproFF2 (manufactured by REPROCELL Inc.), PSGro hESC/iPSC Medium (manufactured by System Biosciences, LLC), NutriStem (registered trademark) Medium (manufactured by Biological Industries), CSTI-7 Medium (manufactured by Cell Science & Technology Institute, Inc.), MesenPRO RS Medium (manufactured by Gibco), MF-Medium (registered trademark) mesenchymal stem cell growth medium (manufactured by TOYOBO), Sf-900II (manufactured by Invitrogen), and Opti-Pro (manufactured by Invitrogen).

When the culture target is cells derived from plants, examples of the culture medium component of the culture medium that is used in the cell culturing method according to the present disclosure include culture media in which a plant growth regulator (plant hormone) such as auxins and, if necessary, cytokinins is added, at a suitable concentration, to basal media such as Murashige Skoog (MS) medium, Linsmaier Skoog (LS) medium, White's medium, Gamborg B5 medium, Nitsch medium, Heller medium, and Morel medium, which are usually used for plant tissue culture, or modified culture media obtained by modifying those medium components to the optimal concentration (for example, reducing the ammonia nitrogen concentration to half). These culture media can be additionally supplemented with, for example, caseinolytic enzymes, corn steep liquor, and vitamins, if necessary. Examples of the auxins include 3-indoleacetic acid (IAA), 3-indolebutyric acid (IBA), 1-naphthaleneacetic acid (NAA), and 2,4-dichlorophenoxyacetic acid (2,4-D), but are not limited thereto. The auxins can be added to a culture medium at a concentration of, for example, approximately 0.1 ppm to approximately 10 ppm. Examples of the cytokinins include kinetin, benzyladenine (BA), and zeatin, but are not limited thereto. The cytokinins can be added to a culture medium at a concentration of, for example, approximately 0.1 ppm to approximately 10 ppm.

Those skilled in the art may freely add, according to the purpose, sodium, potassium, calcium, magnesium, phosphorus, chlorine, various amino acids, various vitamins, antibiotics, serum, fatty acid, and sugar to the culture medium that is used in the cell culturing method according to the present disclosure. In animal-derived cell and/or tissue culture, those skilled in the art can also add one or more other chemical components or biological components in combination according to the purpose. Examples of the components to be added to an animal-derived cell culture medium include fetal bovine serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various hormones, various growth factors, various extracellular matrix, and various cell adhesion molecules.

[Cells to be Cultured]

Cells to be subjected to the cell culturing method according to the present disclosure are not particularly limited and examples thereof include cells that can be suspension-cultured. In one or more embodiments, said cells may include cells derived from animals and cells derived from plants. The cell culturing method according to the present disclosure makes it possible to perform suspended cell culture in which both a suppression of physical stress on cells and an improvement in oxygen supply are achieved. Therefore, cells that are sensitive to physical stress, such as cells that are used for regenerative medicine and plant cells, can also be subjected to the cell culturing method.

In one or more embodiments, cells to be subjected to the cell culturing method according to the present disclosure include cells in cell clusters, spheres, or tissues. In one or more embodiments, therefore, the cell culturing method according to the present disclosure is also a method of culturing cell clusters, spheres, or tissues.

Examples of the cells derived from animals may include germ cells such as sperms and ova, somatic cells constituting a living body, stem cells, progenitor cells, cancer cells isolated from a living body, cells (cell lines) that have been isolated from a living body and have acquired immortalizing ability to be stably maintained outside the body, cells isolated from a living body and artificially genetically modified, and cells isolated from a living body and subjected to artificial nucleus replacement. Examples of the cells derived from plants include cells isolated from each tissue of a plant body and also include protoplasts obtained by artificially removing cell walls from said cells.

In one or more embodiments, examples of the cells to be subjected to the cell culturing method according to the present disclosure include pluripotent stem cells such as embryonic stem cells (ES cells) and induced pluripotent stem cells (iPS or multipotent stem cells such as mesenchymal stem cells, hematopoietic stem cells, and tissue stem cells.

[Arrangement of Cells]

The cell culturing method according to the present disclosure includes arranging cells in a culture medium which is a plastic fluid. Arranging cells includes bringing the cells into a state of being suspended in said culture medium or bringing the cells into a state of being dispersed in said culture medium. In one or more embodiments, this step can be carried out by the following method, but the arrangement method is not limited thereto. As a first example thereof, cells are dispersed in a liquid culture medium before the specific compound or a solution or dispersion thereof is mixed into the liquid culture medium. As a further example of the arrangement method, cells or a dispersion thereof are/is mixed into a mixture of the specific compound, culture medium component, and water to be dispersed therein.

The cells arranged in the culture medium which is a plastic fluid are maintained in a state of being prevented from sedimenting (that is, in a suspended state).

In the cell culturing method according to the present disclosure, the cells to be arranged in the culture medium at the start of culture may be in the form of cells alone, cell clusters, spheres, or tissues obtained by being separately prepared or cultured.

[Introduction of Air Bubbles]

The cell culturing method according to the present disclosure includes introducing air bubbles into a culture medium which is a plastic fluid, in which cells are arranged, to supply oxygen to the cells to be cultured.

The rising speed of the air bubbles introduced into the plastic fluid is suppressed compared to that of air bubbles introduced into a liquid which is not a plastic fluid. This means that the residence time of air bubbles in the plastic fluid is extended and thereby the gas holdup increases. Therefore, the introduction of air bubbles can be reduced to the extent that oxygen required for cell growth can be supplied. Air bubbles may be introduced continuously or intermittently as long as oxygen required for cell growth can be supplied.

[Air Bubbles]

The size of air bubbles to be introduced is preferably small from the viewpoint of reducing the physical stress caused by bubbling and reducing the rising speed, and microbubbles or submicrobubbles are preferred. The diameter of the air bubbles is, for example, 500 μm or less, 100 μm or less, 50 μm or less, 25 μm or less, or 10 μm or less, and 0.1 μm or more, 1 μm or more, or 10 μm or more.

[Method of Introducing Air Bubbles]

The method of introducing air bubbles is not limited but a sparger for culture can be used. Furthermore, a nozzle capable of introducing air bubbles may be used. Air bubbles may be introduced from a single point or from multiple points. The amount of air bubbles to be introduced can be suitably adjusted according to the relationship between the introduction point and the volume of the culture medium.

[Stirring]

The movement of air bubbles introduced into a plastic fluid is temporary and local flow. The portion other than that in which the air bubbles rise does not flow, and the convection caused by the rising of the air bubbles is also suppressed. In one or more embodiments, therefore, in the cell culturing method according to the present disclosure, the culture medium may be stirred at regular intervals to equalize the oxygen supply. Said stirring can be performed at low frequency in a range that results in a physical damage to the extent of not affecting cell growth. The stirring may be performed continuously or intermittently. The stirring frequency can be suitably adjusted according to the amount of air bubbles to be introduced and the relationship between the introduction point and the volume of the culture medium.

Air bubbles can be introduced from multiple points to omit the stirring step.

The method of stirring is not particularly limited and may be stirring with stirring blades, stirring by shaking a whole culture vessel, or a combination thereof. Examples of shaking a whole culture vessel include swinging or rotating the culture vessel.

[Volume of Culture Medium]

The volume of the culture medium in the cell culturing method according to the present disclosure is not limited but can be several liters to several thousands of liters, for example, 3 liters or more, 5 liters or more, 7 liters or more, 9 liters or more, 11 liters or more, 13 liters or more, or 15 liters or more. The upper limit is, for example, 10000 liters or less. As described above, the cell culturing method of the present disclosure makes it possible to culture cells with a large volume of culture medium.

Furthermore, the cell culturing method according to the present disclosure makes it possible to perform mass culture of cells that are sensitive to physical stress (for example, stem cells that are used for regenerative medicine and plant cells), which are difficult to be cultured due to physical stress in a conventional mass culture method.

This is because the technique of introducing air bubbles into a plastic fluid makes it possible to achieve both a suppression of physical stress on cells and an improvement in oxygen supply.

[Culture System]

In one or more embodiments, the cell culturing method according to the present disclosure is preferably performed in a closed-system culture system, for example, a closed-system culture vessel, a culture bag, a bioreactor, or a culturing device, from the viewpoint of preventing, for example, contamination.

The present disclosure may relate to the following embodiments.

[1] A cell culturing method, including arranging cells in a dispersed state in a culture medium which is a plastic fluid and introducing air bubbles into said culture medium.

[2] The cell culturing method according to item [1], wherein the cells are arranged in a dispersed state in the culture medium which is a plastic fluid.

[3] The cell culturing method according to item [1] or [2], wherein the cells can be suspension-cultured.

[4] The cell culturing method according to any one of items [1] to [3], wherein the cells are pluripotent stem cells or multipotent stem cells.

[5] The cell culturing method according to any one of items [1] to [4], wherein the culture medium which is a plastic fluid is a culture medium that can maintain the cells in the culture medium without allowing them to sediment in a static state.

[6] The cell culturing method according to any one of items [1] to [5], including culturing the cells using a cell culture vessel or a cell culture bag.

[7] The cell culturing method according to any one of items [1] to [6], wherein the air bubbles are introduced intermittently or continuously.

[8] The cell culturing method according to any one of items [1] to [7], wherein the air bubbles are microbubbles or submicrobubbles.

[9] The cell culturing method according to any one of items [1] to [8], further including stirring the culture medium intermittently or continuously.

[10] The cell culturing method according to item [9], wherein the stirring is stirring with a stirring blade or stirring by shaking a whole culture vessel.

[11] The cell culturing method according to any one of items [1] to [10], wherein the culture medium has a yield value of at least 0.03 Pa.

Examples

Hereinafter, the present disclosure will be described in more detail using experiment examples, which, however, are illustrative and the present disclosure is not limited to these experiment examples.

[Materials and Experimental Method]

1. Cells and Culture Medium Used, Reagent Used, and Culture Conditions 1.1 Cells Used Human induced pluripotent stem cells (hereinafter referred to as hiPS cells, Tic strain, National Center for Child Health and Development) were used for the experiments. The hiPS cells were those obtained by being subcultured multiple times on the iMatrix-511 (manufactured by Nippi, Inc.) coated surface.

1.2 Culture Medium Used

The culture medium used herein was mTeSR™ 1 (manufactured by STEMCELL Technologies Inc., hereinafter referred to as "mTeSR1") (hereinafter referred to as a normal culture medium).

1.3 Reagent Used

A compound A, deacylated gellan gum (manufactured by Nissan Chemical Industries, Ltd.), or a compound B, xanthan gum (manufactured by Sigma-Aldrich), was used as a compound for forming a plastic fluid.

1.4 Culture Conditions

Culture was performed in a $CO_2$ incubator (MCO-17AI, manufactured by SANYO Electric Co., Ltd.) under the conditions of 37° C. and 5% $CO_2$.

2. Preparation of Plastic Fluid Culture Medium

The compound A and B (mentioned above) for forming a plastic fluid each were dissolved in the normal culture medium to have a predetermined concentration (mass/volume %, hereinafter simply referred to as "%"). Thus, plastic fluid culture media were prepared.

3. Culture 3.1 Three-Dimensional Suspension Culture of hiPS Cells with Sparging

The hiPS cells precultured on the iMatrix-511 coated surface were washed with PBS. To EDTA adjusted to 5 mM with PBS, 55 µl of EDTA/PBS solution containing 10 µM of Rock inhibitor added thereto was added per 1 $cm^2$ of culture area, which then was allowed to stand at room temperature for ten minutes. Thereafter, 55 µl of TrypLE Select solution containing 10 µM of Rock inhibitor added to TrypLE Select was added per 1 $cm^2$ of culture area, which then was allowed to stand at room temperature for seven minutes. 55 µl of normal culture medium was added per 1 $cm^2$ to perform enzyme neutralization and then monodispersed hiPS cells were recovered. They were centrifuged at 170×g at room temperature for three minutes, and the supernatant liquid was removed. Then, the normal culture medium was added thereto again to resuspend the cells, to which a Rock inhibitor adjusted to 10 µM was added. Thus, a cell suspension was prepared. This was adjusted to $1.0 \times 10^5$ cells/ml, seeded in 30-ml single-use bioreactor BWV-S03A (manufactured by Able Co.), and cultured for 24 hours to form cell clusters. Thereafter, they were cultured up to 120 hours under the following two conditions.

Culture Control

As a control, suspension culture was performed using a normal culture medium while the medium was replaced with a normal culture medium every 24 hours from 24 hours after the start of the culture.

Suspension Culture with Sparging

The medium was replaced, every 24 hours from 24 hours after the start of the culture, with a plastic fluid culture medium (a plastic fluid culture medium A, the same applies hereinafter) containing a compound A added to a normal culture medium to have a concentration of 0.02%. During the culture period, sparging was performed at a flow rate of 0.01 ml/min using a $CO_2$ Gas Mixer (manufactured by Tokken, inc.). In the suspension culture using the plastic fluid culture medium A, stirring blades were intermittently rotated at 30 rpm to perform stirring.

3.2 Measurement of Cell Concentration

The cell concentration was measured every 24 hours. Sampling of 250 µl was performed in a centrifuge tube, three times. Samples cultured in the normal culture medium were centrifuged at 170×g for three minutes and then the supernatant was removed. Thereafter, 5 ml of Accumax (manufactured by Innovative Cell Technologies) was added thereto, which was reacted at room temperature for ten minutes and thus monodisperse treatment was performed. For samples cultured in the plastic fluid culture medium A, PBS was added thereto to dilute them 5-fold, followed by centrifugation at 170×g for three minutes. After removal of the supernatant, 5 ml of Accumax was added thereto, which was reacted at room temperature for ten minutes and thus monodisperse treatment was performed. Thereafter, this was centrifuged again at 170×g and then the supernatant was removed. Then, a normal culture medium was added thereto, resulting in resuspension. Live cell concentration was measured by the trypan blue dye exclusion method using a TC20™ automated cell counter (manufactured by Bio-Rad Laboratories, Inc.).

4. Observation of Effects Obtained by Using Plastic Fluid Culture Medium 4.1 Observation of Effects on Air Bubble Rising A plastic fluid culture medium A and a normal culture medium were sparged at a flow rate of 0.01 ml/min using the $CO_2$ gas mixer. This was observed using a video camera (HDR-CX 420, manufactured by SONY Corporation).

4.2 Observation of Effects on Cell Clusters

Pipetting was performed on a plastic fluid culture medium A and a normal culture medium, and the states thereof were observed using the video camera. The cell clusters contained in the culture media used herein were cultured for 120 hours in the same manner as that used for the control in 3.1 and then recovered.

4.3 Observation of Effects on Liquid Flow

A plastic fluid culture medium A and a normal culture medium were sparged at a flow rate of 0.01 ml/min using the $CO_2$ gas mixer. This was observed using the video camera. The cell clusters contained in the culture media used herein were cultured for 120 hours in the same manner as that used for the control in 3.1 and then recovered.

[Results and Discussion]

1. Physical Properties of Plastic Fluid

The compound A or B was dissolved in a normal culture medium so as to have a concentration (mass/volume %) indicated in Table 1 below and thereby respective liquid compositions were prepared. The following two physical properties of said liquid compositions were examined. The results are indicated in Table 1 below.

(1) Bead Retention

Polystyrene beads (Positive Charged Microcarriers, manufactured by Corning Incorporated, particle size 160 to 200 µm, density 1.09 to 1.15 $g/cm^3$) used as mock cells were suspended in said liquid compositions, which then were allowed to stand at 37° C. The state of the beads was observed 24 hours after the start of suspension taken as the starting point.

(2) Air Bubble Retention

Air bubbles were enclosed in said liquid compositions by pipetting, which then were allowed to stand at 37° C. The state of the air bubbles was observed 24 hours after the start of suspension taken as the starting point.

(3) Measurement of Yield Value

The yield values of said liquid compositions at 37° C. were measured using a rheometer (trade name MCR 302, manufactured by Anton Paar GmbH).

As indicated in Table 1 below, the normal culture medium (liquid composition) containing the compound A added thereto allowed the beads to be maintained (bead sedimentation to be suppressed) when the content of the compound A was 0.02% or more, and exhibited the physical properties of a plastic fluid. In addition, as a result of suppressing the rising speed of air bubbles, retention of air bubbles was observed when the content of the compound A was 0.04% or more. The yield value was able to be measured when the content of the compound A was 0.03% or more, and the yield value at 0.03% was 0.030 Pa. The yield value of the liquid composition containing 0.02% or less of the compound A was below the detection sensitivity of the rheometer used herein.

Figure 1:
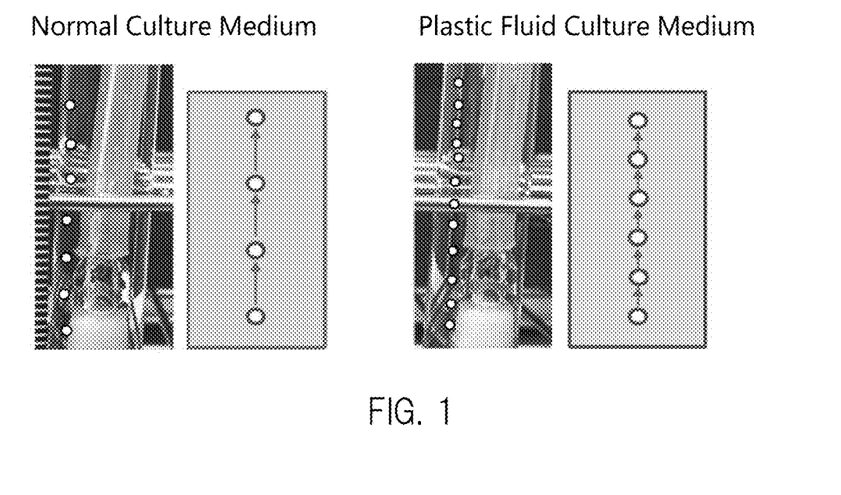
FIG. 1 shows examples of the results of examining the air bubble rising speed in a Newtonian fluid (a normal culture medium) and a plastic fluid culture medium A.

Furthermore, as indicated in Table 1 below, the normal culture medium (liquid composition) containing the compound B added thereto allowed the beads to be maintained (bead sedimentation to be suppressed) when the content of the compound B was 0.3% or more, and exhibited the physical properties of a plastic fluid. In addition, as a result of suppressing the rising speed of air bubbles, retention of air bubbles was observed when the content of the compound B was 0.5% or more. The yield value was able to be measured when the content of the compound B was 0.4% or more, and the yield value at 0.4% was 0.036 Pa. The yield value of the liquid composition containing 0.3% or less of the compound B was below the detection sensitivity of the rheometer used herein.

fluid culture medium A than in the normal culture medium and thereby it was confirmed that the air bubbles rose slowly in the plastic fluid culture medium A. Table 2 shows the average air bubble rising speed measured from the video of this experiment. From these results, it is suggested that the use of a plastic fluid makes it possible to suppress the rising speed of air bubbles and retain them in the liquid for a long time to increase gas holdup.

TABLE 2

| Rising Speed of Air Bubbles | | |
| --- | --- | --- |
|  | Normal Medium | Plastic Fluid Culture Medium A |
| Rising Speed of Air Bubbles (cm/s) | 4.29 | 2.55 |

3. Effects of Plastic Fluid on Cell Clusters

Figure 2:
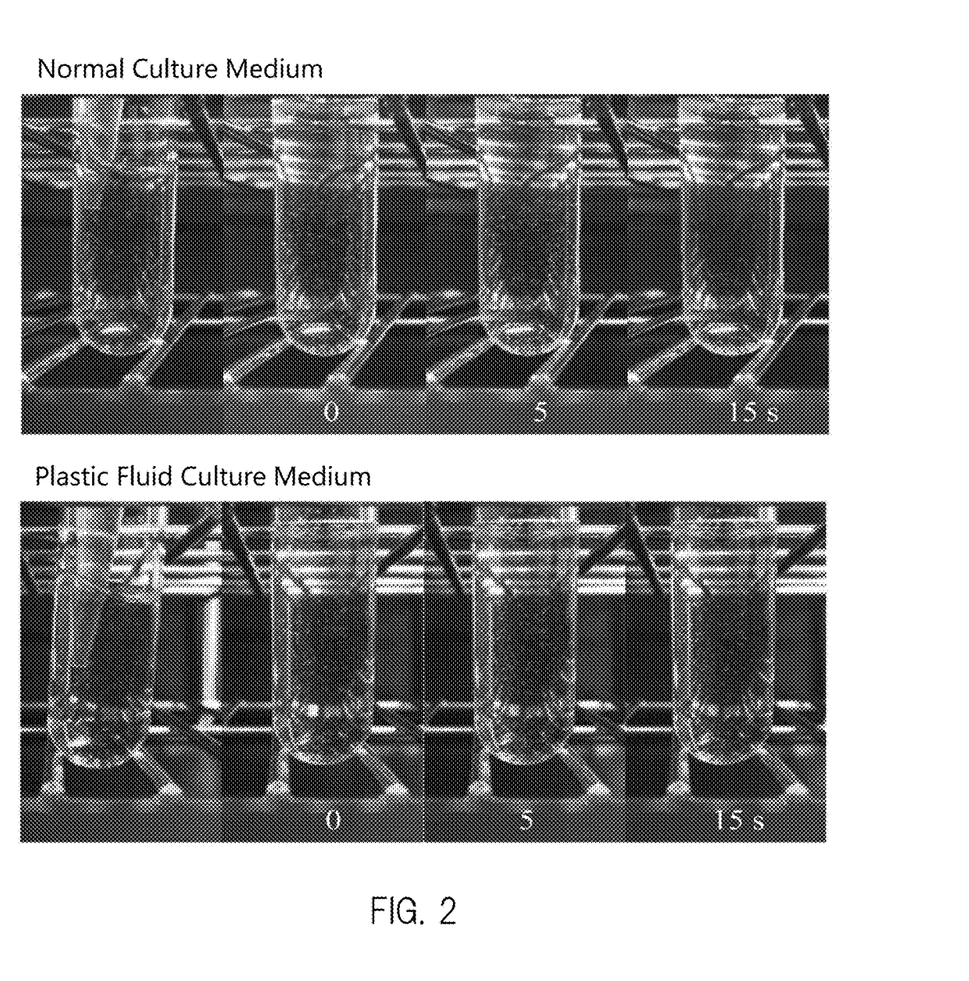
FIG. 2 shows examples of the results of examining the dispersion state of cell clusters in a Newtonian fluid (a normal culture medium) and a plastic fluid culture medium A.

Pipetting was performed on a plastic fluid culture medium A and a normal culture medium that contain cell clusters, and the states thereof were observed. FIG. 2 shows the images taken at the time of pipetting, at the end of pipetting, as well as 5 seconds and 15 seconds after the end of pipetting in each medium. From these images, it was confirmed that in the plastic fluid culture medium A, the cell clusters uniformly diffused in the culture medium by pipetting were maintained in the culture solution, while they were sedimented in the normal culture medium. Thus, it is suggested that when a plastic fluid is used, the culture solution can be stirred to generate a liquid flow under a shear stress environment, while under a shearless (shear stress is absent or suppressed) environment, the liquid flow generated by pipetting is stopped quickly and cell clusters can be maintained in the liquid.

4. Effects of Plastic Fluid on Liquid Flow

One deep aeration device was used to sparge a plastic fluid culture medium A at an airflow rate of 0.01 ml/min, and the state thereof was observed. Images, taken between 0.00 to 6.00 seconds, of the vicinity of the air bubble rising portion (FIG. 3) and a position slightly away therefrom

TABLE 1

| Compound A for Forming Plastic Fluid | | | | Compound B for Forming Plastic Fluid | | | |
| --- | --- | --- | --- | --- | --- | --- | --- |
| Concentration | Beads | Air Bubbles | Yield Value (Pa) | Concentration | Beads | Air Bubbles | Yield Value (Pa) |
| 0.01 | Sedimented | Rose and disappeared | —*1 | 0.2 | Sedimented | Rose and disappeared | —*1 |
| 0.02 | Maintained | Rose and disappeared | —*1 | 0.3 | Maintained | Rose and disappeared | —*1 |
| 0.03 | Maintained | Rose and disappeared | 0.030 | 0.4 | Maintained | Rose and disappeared | 0.036 |
| 0.04 | Maintained | Retained | 0.040 | 0.5 | Maintained | Retained | 0.041 |
| 0.05 | Maintained | Retained | 0.049 | 0.6 | Maintained | Retained | 0.095 |

Concentration: Mass/Volume Percent
*1Below the detection sensitivity

2. Effects of Plastic Fluid on Air Bubble Rise

Figure 3:
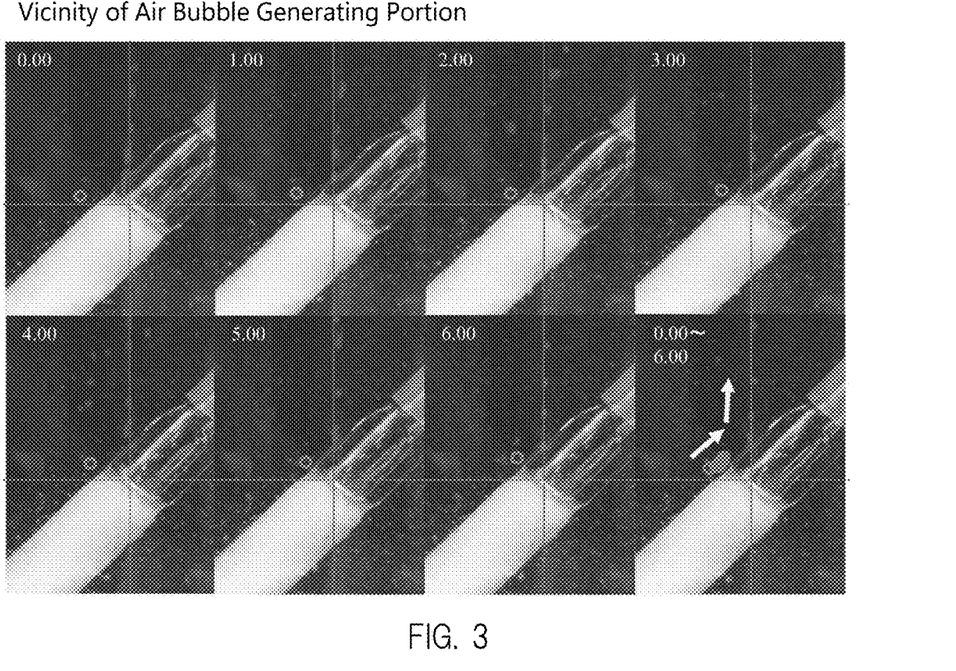
FIG. 3 shows an example of the result of examining the behavior (○) of the cells in the vicinity of the air bubble rising portion in the case where air bubbles were introduced (sparged) into the plastic fluid culture medium A.
Figure 4:
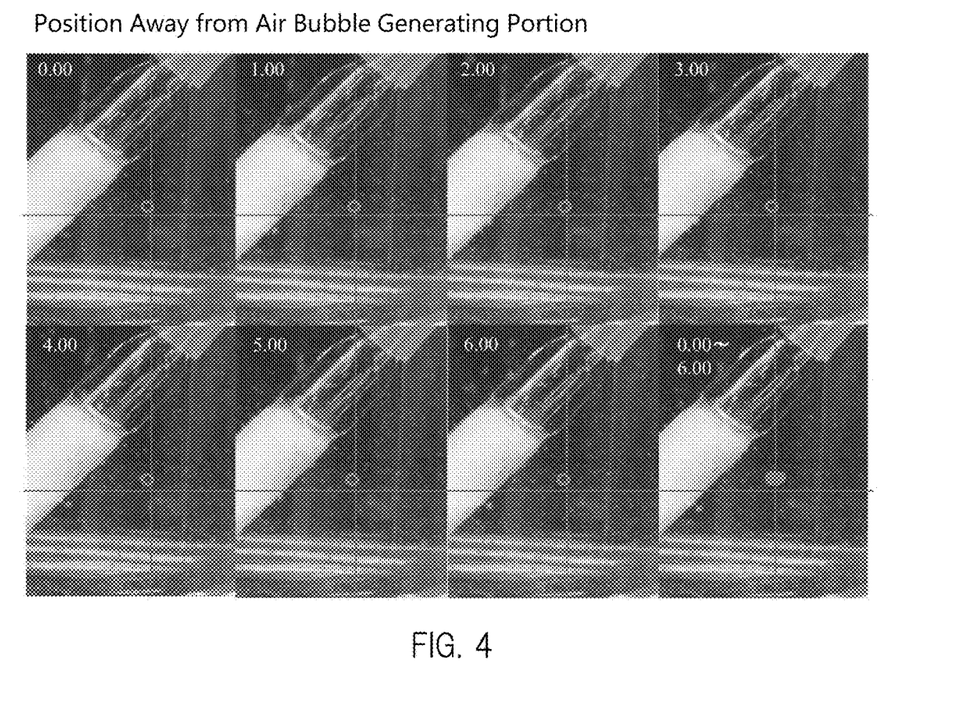
FIG. 4 shows an example of the result of examining the behavior (○) of the cells at a position slightly away from the vicinity of the air bubble rising portion in the case where air bubbles were introduced (sparged) into the plastic fluid culture medium A.

Using a deep aeration device, a plastic fluid culture medium A (0.02% compound A) and a normal culture medium were sparged at a flow rate of 0.01 ml/min, and the states thereof were observed. FIG. 1 shows, with dots, the positions of air bubbles that were obtained by checking the rise of the air bubbles at 0.1 second intervals, respectively. From the images, the distance between the air bubbles checked at 0.1 second intervals was shorter in the plastic (FIG. 4) in the same vessel are shown. The circles in the images show the same cluster at the centers thereof. As shown in the images, it was observed that the cell cluster also rose along the liquid flow in the vicinity of the air bubble rising portion. On the other hand, it was observed that the cell cluster hardly moved and was maintained in a static state at the position slightly away. Therefore, it is suggested that the rising flow accompanying the air bubble rising was generated only in the vicinity of the air bubble rising portion and convection generated by the rising flow is also suppressed at the position slightly away in the Newtonian fluid.

5. Suspension Culture with Sparging

The experiments above confirmed that the use of a plastic fluid suppressed liquid flow and thereby prevented convection from being generated, when sparging was performed. Thus, it is expected that when sparging is performed only from one point, sufficient oxygen is supplied only in the vicinity of the air bubble rising portion and oxygen depletion occurs at the positions away therefrom. Therefore, it is considered to be necessary to perform stirring at low frequency for a short time to create a uniform environment. Thus, while the plastic fluid culture medium A was sparged, stirring was performed for five minutes every eight hours to culture hiPS cell clusters. It is considered that a uniform environment can also be created by increasing the number of sparging points instead of stirring performed at low frequency for a short time.

5.1 Form of Cell Clusters

Figure 5:
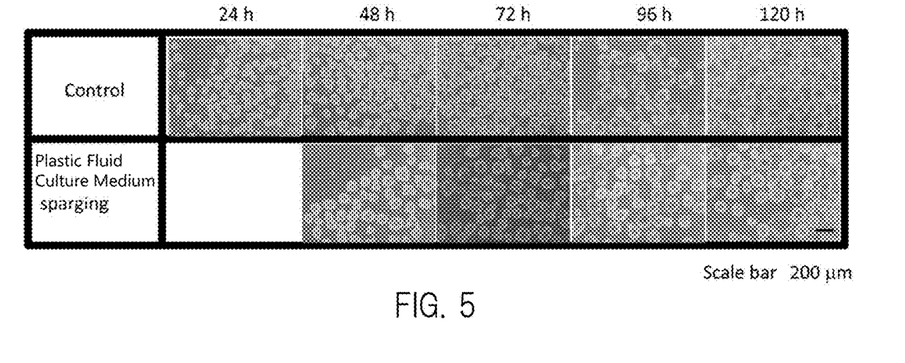
FIG. 5 shows representative images (captured at different times) of cell clusters in a culture solution in which cells were suspension-cultured while air bubbles were introduced (sparged) into a control culture medium and the plastic fluid culture medium A.

FIG. 5 shows representative images captured at respective times of suspension culture in which a control and a plastic fluid culture medium A were sparged. As a result, it was observed that even in the suspension culture with sparging, the cluster diameter increased as in the suspension culture in the normal culture medium which is the control.

5.2 Time Course of Cell Concentration

Figure 6:
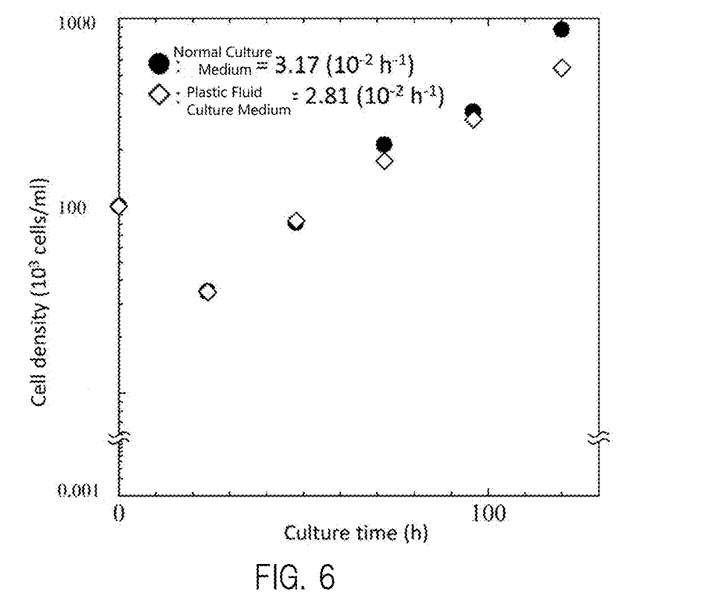
FIG. 6 shows an example of the time course of the cell concentration in the culture solution in which cells were suspension-cultured while air bubbles were introduced (sparged) into the control culture medium (●) and the plastic fluid culture medium A (◇).

FIG. 6 shows the time course of cell concentration. This result confirmed that even when being sparged, the plastic fluid culture medium A allowed hiPS cells, which are animal cells, to grow as in the suspension culture in the normal culture medium. The above results suggested that oxygen supply by sparging becomes possible even in bioreactors of larger scale. On the other hand, in the case of suspension culture in the normal culture medium (that is, in the case of supplying oxygen only by surface aeration), the gas-liquid interfacial area per unit volume decreases as the culture solution volume increases. Therefore, it is considered that sufficient oxygen cannot be supplied in the culture in which the culture medium is used in a large volume such as several to several tens of liters or more.

6. Confirmation of Oxygen Supply and Cell Growth Under Different Yield Value Conditions The compound A was dissolved in a normal culture medium so as to be 0.02% and 0.05%, thereby preparing two plastic fluid culture media having different yield values (Table 1 above). For each solution, air bubbles with non-uniform diameters were enclosed in the solution by a pipetting operation, and then cell clusters pre-cultured for 120 hours were suspended at a seeding density of $4.0 \times 10^5$ cells/mL. Thereafter, the 30-ml single-use bioreactor (same as above) was used to perform culture in a 37° C. incubator. The cell density was measured every six hours of culture and the transition of cell density over time was measured up to 24 hours of culture. The results are shown in FIGS. 7 and 8.

Figure 7:
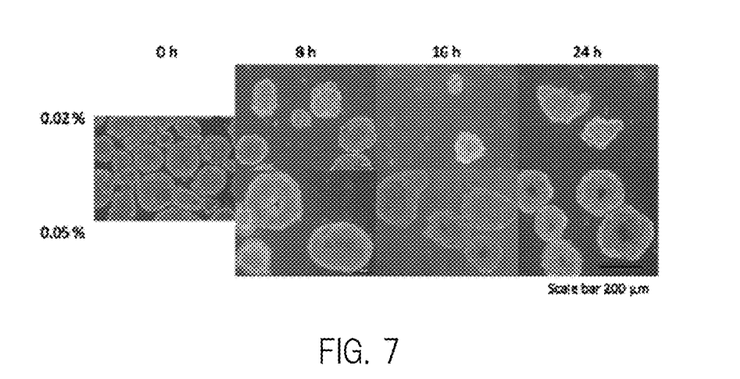
FIG. 7 shows examples of microscopy images of cell clusters, which show the result of checking oxygen supply and cell growth under conditions of different yield values.
Figure 8:
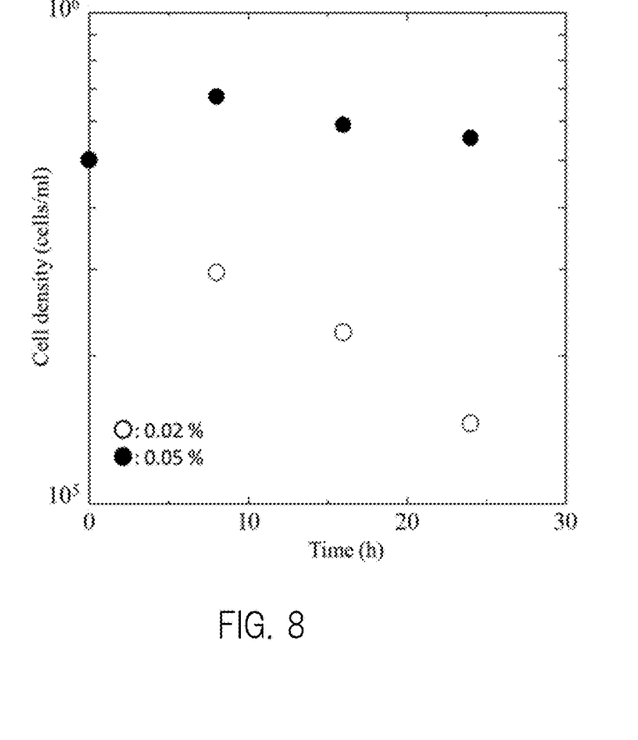
FIG. 8 shows an example of a time-course graph of the cell density of the cell clusters, which shows the result of checking oxygen supply and cell growth under the conditions of different yield values.

FIG. 7 shows the states of cell clusters over time. FIG. 8 shows the states of cell density over time.

Under the concentration condition (the compound A 0.02%) where air bubbles are not retained in the liquid, it was confirmed that the cell cluster diameter tended to decrease and the contours of the cell clusters tended to change from a smooth shape to a distorted shape over time. In addition, the cell density also decreased with time. On the other hand, under the concentration condition (the compound A 0.05%) where air bubbles retained in the liquid were observed, the cell cluster diameter and the cell density tended to be maintained. Table 3 below shows the results of the viability a after 24 hours of culture calculated from the result of the cell density.

TABLE 3

| Viability after 24 hours | |
|---|---|
| Concentration of Compound A | Viability α |
| 0.02% | 0.29 |
| 0.05% | 1.11 |

Viability α is represented by the following formula using the seeding density $X_0$ (cells/mL) and the cell density $X_{24}$ (cells/mL) obtained after 24 hours of culture.

$$\alpha = \frac{X_{24}}{X_0}$$

Whereas the cell density and the viability tended to decrease under the concentration condition (the compound A 0.02%) where air bubbles were not retained, an initial increase in cell density and maintenance thereof thereafter were observed under the concentration condition (the compound A 0.05%) where air bubbles were retained. Thus, it was confirmed that the use of the plastic fluid culture medium allowed air bubbles to be retained in the liquid to supply oxygen.

Figure 9:
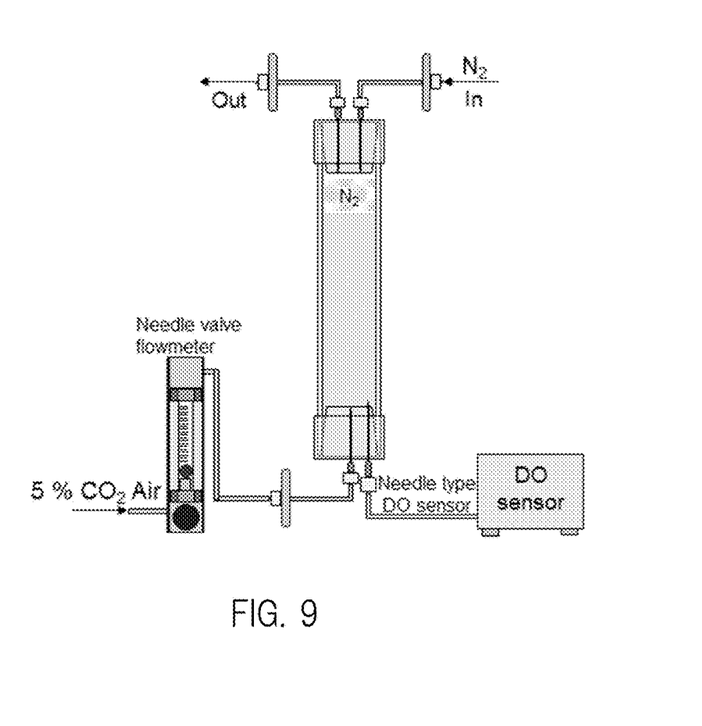
FIG. 9 shows a schematic view of a culturing device that allows oxygen to be supplied only from sparging.

7. Plastic Fluid Suspension Culture Under Conditions where Oxygen Supply is Limited to Sparging A device was constructed in which oxygen is supplied only from air bubbles (sparging) supplied into the liquid as shown in FIG. 9. In the device, continuous aeration with nitrogen is performed from the upper part of the device to allow the space above the liquid to be subjected to nitrogen substitution, and oxygen is supplied only from air bubbles that are supplied into the liquid through one nozzle disposed in the lower part. In this device, cell culture accompanied by air bubble aeration is performed to allow cell culture to be achieved under oxygen supply by air bubble aeration (sparging).

An experiment was conducted according to the experimental outline described below. The hiPS cells (D2) precultured on a two-dimensional surface were treated with 5 mM EDTA/PBS and TrypLE™ Select to be detached from the culture surface and to be monodispersed. The cell suspension was adjusted to have a seeding density of $1.0 \times 10^5$ cells/mL using StemFit™ AK02N adjusted to contain 10 mM of Rock inhibitor Y-27632, and was seeded in a single use bioreactor 30 mL to be precultured for 48 hours. After 48 hours, cell clusters were recovered and then were seeded in a compound A-containing plastic culture medium. Culture was performed under two conditions: a condition where sparging was performed and a condition as a control where sparging was not performed. In both conditions, culture was performed under the condition where the part above the culture solution was always aerated with nitrogen gas to be subjected to nitrogen substitution. The cell density was measured after 24 hours of culture. The results are shown in FIGS. 10 and 11.

[Experimental Outline]
Cells: Human induced pluripotent stem cells (hiPS cells, D2)
Culture Medium: StemFit™ AK02N (Ajinomoto)
Culture Vessel: Single-use bioreactor 100 mL (Able. Co., Cat. No. BWV-S10A)
:Single nozzle bioreactor (Fujimori Kogyo)
Gas Composition: 5% $CO_2$ Air
Measurement Environment: Inside of 37° C. incubator
Working Volume: 90 mL Observation Period: 24 h
Reagent Used: TrypLE™ Select (1×) (Gibco)
:Rock inhibitor Y-27632 (Sigma)
:Ethylenediamine-N,N,N',N'-tetraacetic acid, disodium salt, dihydrate (EDTA, Dojindo)
:Compound A: 0.05%

Figure 10:
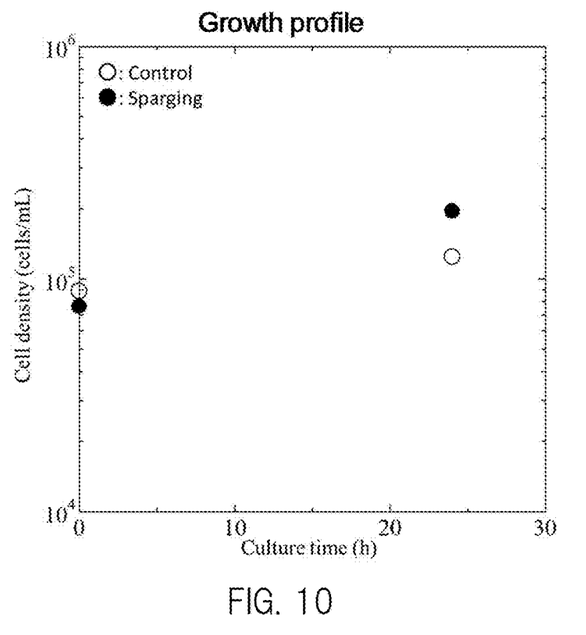
FIG. 10 shows an example of a graph illustrating the result of cell densities obtained after 24 hours in culture with sparging and control culture without sparging in the culturing device of FIG. 9.
Figure 11:
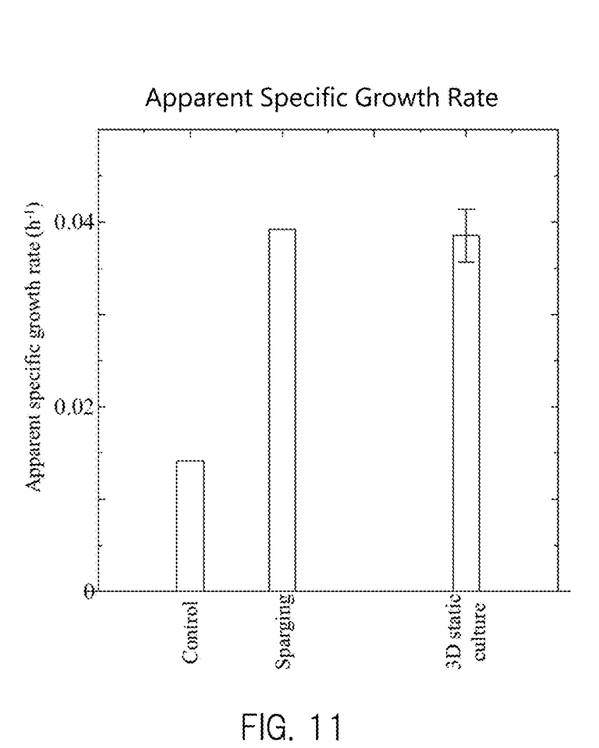
FIG. 11 shows an example of a graph comparing the apparent specific growth rates up to 24 hours in the culture with sparging and the control culture without sparging in the culturing device of FIG. 9 as well as three-dimensional static culture.

As shown in FIG. 10, the cell density was high after 24 hours of culture under the condition where sparging was performed as compared with the control condition where sparging was not performed. Furthermore, as shown in FIG. 11, the specific growth rate $\mu^{app}$ ($h^{-1}$) up to 24 hours of culture under the condition where sparging was performed was higher as compared to the control and was almost the same as the apparent specific growth rate of 3D static culture. From these results, it was assumed that under the control condition, oxygen was insufficient for cell growth and thereby the growth rate decreased. It was confirmed that the use of the plastic fluid culture medium made it possible to supply oxygen to the hiPS cell culture system by sparging. In this case, since the plastic fluid culture medium showed almost the same specific growth rate as that of the 3D static culture, it was confirmed that shear stress caused by sparging was suppressed in the plastic fluid.

Therefore, the cell culturing method according to the present disclosure makes it possible to perform suspended cell culture in which both a suppression of physical stress on cells and an improvement in oxygen supply are achieved. It is considered that according to the cell culturing method of the present disclosure, even in the suspended cell culture using a culture medium in a large volume such as several to several tens of liters or more, it is possible to achieve both a suppression of physical stress on cells and an improvement in oxygen supply, which makes it possible to mass-culture cells that are sensitive to physical stress, such as cells that are used for regenerative medicine and plant cells.

The invention claimed is:

1. A cell culturing method, comprising:
arranging cells in a culture medium which is a plastic fluid so as to be suspended in the medium in a static state;
culturing the cells in a suspended state; and
introducing air bubbles into said culture medium and suppressing the rising speed of the air bubbles while maintaining the suspended state; wherein the cells are pluripotent stem cells or multipotent stem cells.

2. The cell culturing method according to claim 1, wherein the culture medium which is a plastic fluid is a culture medium that can maintain the cells in the culture medium without allowing them to sediment in a static state.

3. The cell culturing method according to claim 1, comprising culturing the cells using a cell culture vessel or a cell culture bag.

4. The cell culturing method according to claim 1, wherein the air bubbles are introduced intermittently or continuously.

5. The cell culturing method according to claim 1, wherein the air bubbles are microbubbles or submicrobubbles.

6. The cell culturing method according to claim 1, wherein the culture medium has a yield value of at least 0.04 Pa.

* * * * *